United States Patent [19]

Ohashi et al.

[11] Patent Number: 4,861,877
[45] Date of Patent: Aug. 29, 1989

[54] PROCESS FOR PREPARING 4-ACETOXY-3-HYDROXYETHYLAZETIDIN-2-ONE DERIVATIVES

[75] Inventors: Takehisa Ohashi; Kazunori Kan, both of Kobe; Noboru Ueyama; Isao Sada, both of Akashi; Akimasa Miyama, Takasago; Kiyoshi Watanabe, Akashi, all of Japan

[73] Assignee: Kanegafuchi Kagaku Kogyo Kabushiki Kaisha, Osaka, Japan

[21] Appl. No.: 809

[22] Filed: Jan. 6, 1987

Related U.S. Application Data

[63] Continuation-in-part of Ser. No. 750,824, Jul. 1, 1985, abandoned.

[30] Foreign Application Priority Data

Jul. 5, 1984 [JP] Japan ............................. 59-139797
Jan. 14, 1985 [JP] Japan ............................. 60-4724
Jan. 14, 1986 [JP] Japan ............................. 61-5636

[51] Int. Cl.$^4$ .................... C07D 205/08; C07F 7/18; C07B 41/12
[52] U.S. Cl. ............................................. 540/357
[58] Field of Search ..................................... 540/357

[56] References Cited

U.S. PATENT DOCUMENTS 4,474,793 10/1984 Ross et al. ........................ 540/350

FOREIGN PATENT DOCUMENTS 0070204 1/1983 European Pat. Off. .
0078026 5/1983 European Pat. Off. .
0106652 4/1984 European Pat. Off. .
0167154 1/1986 European Pat. Off. .
0181831 5/1986 European Pat. Off. .
0167155 8/1986 European Pat. Off. .
1770855 12/1970 Fed. Rep. of Germany .
2105329 3/1983 United Kingdom ................ 540/310
2144419 3/1985 United Kingdom .

OTHER PUBLICATIONS

Yoshida et al., Chem. Pharm. Bull., vol. 29, pp. 2899–2909, 1981.
Shiozaki et al., Tetrahedron, vol. 39, No. 13, 1983, pp. 2399–2407.
Reider et al., Tetrahedron Letters, vol. 23, No. 22, pp. 2293–2296, 1982.
Fuchs et al., Chem. Ber. 107, pp. 721–724, 1974.
Wetter et al., Tetrahedron Letters, vol. 26, No. 45, 1985, pp. 5515–5518.
Chiba et al., Chemistry Letters, No. 7, 1984, pp. 1927–1930.

*Primary Examiner*—Mark L. Berch
*Attorney, Agent, or Firm*—Armstrong, Nikaido, Marmelstein Kubovcik & Murray

[57] ABSTRACT

A process for preparing a 4-acetoxy-3-hydroxyethylazetidin-2-one derivative having the formula (II):

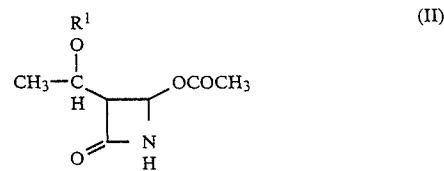

wherein $R^1$ is a protective group for the hydroxyl group, which comprises reacting a β-lactam compound having the formula (I):

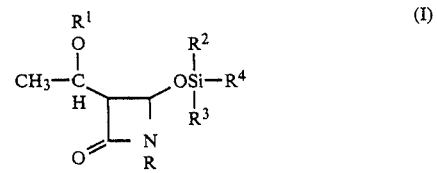

wherein $R^1$ is as defined above, $R^2$, $R^3$ and $R^4$ are a lower alkyl group having 1 to 6 carbon atoms, phenyl group or an aralkyl group and R is a protective group for N, with acetic anhydride in an organic solvent in the presence of a base, and removing the protective group for N.

4-Acetoxy-3-hydroxyethylazetidin-2-one derivatives are useful intermediates for preparing carbapenem β-lactam antibiotics such as thienamycin and penem α-lactam antibiotics.

12 Claims, No Drawings

PROCESS FOR PREPARING 4-ACETOXY-3-HYDROXYETHYLAZETIDIN-2-ONE DERIVATIVES

CROSS-REFERENCE TO RELATED APPLICATION

This is a continuation-in-part of application Ser. No. 750,824 filed on July 1, 1985 abandoned.

BACKGROUND OF THE INVENTION

The present invention relates to a process for preparing 4-acetoxy-3-hydroxyethylazetidin-2-one which has a hydroxyethyl group, wherein the hydroxyl group is protected, at the C3-position and has an acetoxyl group at the C4-position. It is known that 4-acetoxy-3-hydroxyethylazetidin-2-one derivatives are useful intermediates for preparing carbapenem $\beta$-lactam antibiotics such as thienamycin and penem $\beta$-lactam antibiotics (cf., for example, Tetrahedron Letters by Reider et al., vol. 23, page 2293, 1982 and Chem. Pharm. Bull. by Yoshida et al., vol. 29, page 2899, 1981).

There hitherto have been known processes for synthesizing 4-acetoxy-3-hydroxyethylazetidin-2-one derivatives, for instance, synthesis from 6-aminopenicillanic acid (cf. Chem. Pharm. Bull. by Yoshida et al., vol. 29, page 2899, 1981), synthesis from threonine (cf. Tetrahedron by Shiozaki et al, vol. 39, page 2399, 1983) and synthesis from aspartic acid (cf. Tetrahedron Letters by Reider et al., vol. 23, page 2293, 1982). However, these processes have a problem that industrially unfavourable heavy metals such as mercury acetate and lead tetraacetate are employed in order to introduce an acetoxyl group at the C4-position of the $\beta$-lactam ring.

SUMMARY OF THE INVENTION

The inventors found a process for preparing a $\beta$-lactam compound having an O-protected hydroxyethyl group at the C3-position and a silylether group at the C4-position by reaction of enolsilylethers with chlorosulfonylisocyanate, and filed a patent application. The inventors have further found that 4-acetoxy-3-hydroxyethylazetidin-2-one can be easily prepared by using the above-mentioned $\beta$-lactam compound.

According to the present invention, there is provided a process for preparing a 4-acetoxy-3-hydroxyethylazetidin-2-one derivative having the formula (II):

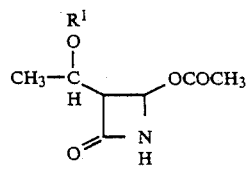

(II)

wherein $R^1$ is a protective group for the hydroxyl group, which comprises reacting a $\beta$-lactam compound having the formula (I):

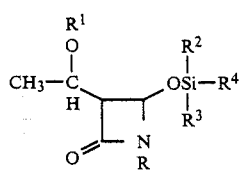

(I)

wherein $R^1$ is a protective group for the hydroxyl group, $R^2$, $R^3$ and $R^4$ are a lower alkyl group having 1 to 6 carbon atoms, phenyl group or an aralkyl group and R is a protective group for N, with acetic anhydride in an organic solvent in the presence of a base, and removing the protective group for N.

DETAILED DESCRIPTION

The $\beta$-lactam compound (I) is prepared by introducing substituent group R at the N-position of a $\beta$-lactam compound having the formula (I'):

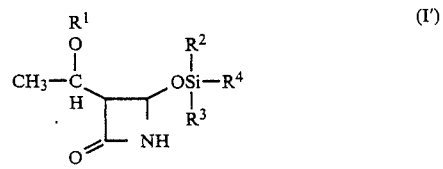

(I')

wherein $R^1$, $R^2$, $R^3$ and $R^4$ are as defined above. As shown in the application of the inventors (Japanese Unexamined Patent Publication No. 139797/1984), the $\beta$-lactam compound (I') having a silylether group at the C4-position can be easily obtained by the process of the following reaction scheme:

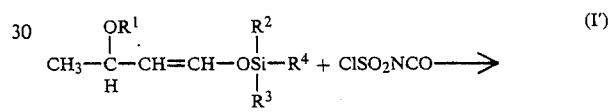

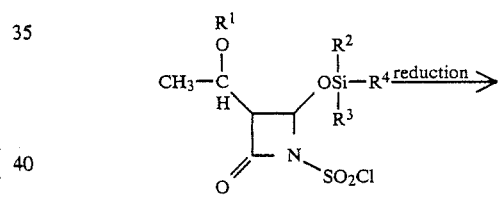

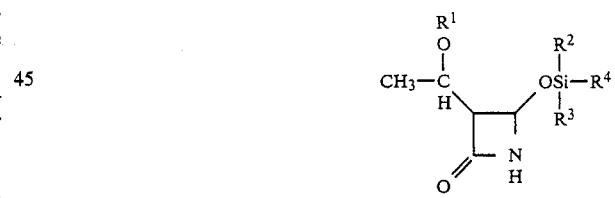

The $\beta$-lactam compound of the formula (I), which has a protective group for N, can be obtained by reaction of the $\beta$-lactam compound having the formula (I') and a reagent having the formula of R—X, wherein R is as above and X is a halogen. Examples of the reagent having the formula of R—X are, for instance, trialkylsilyl halide such as t-butyldimethylsilyl chloride, isopropyldimethylsilyl chloride, isobutyldimethylsilyl chloride, trimethylsilyl chloride and dimethyl-1,1,2-trimethylpropylsilyl chloride, alkyloxyoxalyl chloride, aralkyloxyoxalyl chloride and allyloxyoxalyl chloride such as $$\text{Cl}-\underset{\underset{O}{\|}}{C}-\underset{\underset{O}{\|}}{C}-OCH_3, \quad \text{Cl}-\underset{\underset{O}{\|}}{C}-\underset{\underset{O}{\|}}{C}-OCH_2CH_3,$$

-continued

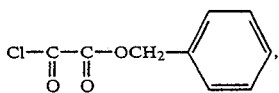

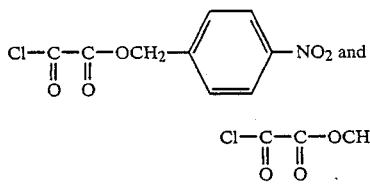

Among them, t-butyldimethylsilyl chloride, whereby t-butyldimethylsilyl group is introduced as a protective group for N in the β-lactam compound (I), is preferable.

Such an introduction of the protective group for N can be, for instance, carried out by subjecting to dehydrogen chloride reaction is reacting the compound (I') with the reagent of the formula of R—X in the presence of a base such as triethylamine or imidazole in a medium such as DMF (dimethylformamide) or methylene chloride, distilling away the medium, extracting the desired compound (I) and distilling away the employed extraction solvent to give a pure compound (I).

Examples of the O-protective group of $R^1$ for the hydroxyl group at the C3-position of the β-lactam compound (I) are, for instance, trialkylsilyl group having the formula (III):

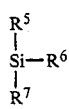 (III)

wherein $R^5$, $R^6$ and $R^7$ are a lower alkyl group having 1 to 6 carbon atoms such as tert-butyldimethylsilyl group, triisopropylsilyl group, isopropyldimethylsilyl group, isobutyldimethylsilyl group, dimethyl-1,1,2-trimethylpropylsilyl group, t-butyl group, benzyl group, trichloroethoxycarbonyl group, tert-butoxycarbonyl group, p-nitrobenzyloxycarbonyl group or the like. Among them, tert-Butyldimethylsilyl group, isopropyldimethylsilyl group and dimethyl-1,1,2-trimethylpropylsilyl group are preferable since they are stable during the reaction and can be selectively removed by acid treatment. Groups $R^2$, $R^3$ and $R^4$ of the β-lactam compound having the formula (I) may be the same or different with each other, and selected from a lower alkyl group having 1 to 6 carbon atoms such as methyl, ethyl, isopropyl, isobutyl, tert-butyl or 1,1,2-trimethylpropyl group, phenyl group, or an aralkyl group such as benzyl group, p-nitrobenzyl group. It is preferred all of $R^2$, $R^3$ and $R^4$ are methyl group.

The β-lactam compound, prepared as mentioned above, having the formula (I):

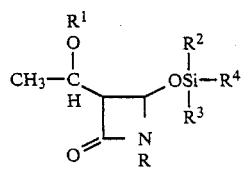 (I)

wherein $R^1$, $R^2$, $R^3$, $R^4$ and R are as defined above, is reacted with acetic anhydride in an organic solvent in the presence of a base to convert the β-lactam compound (I) into the desired 4-acetoxy-3-hydroxyethylazetidin-2-one derivative having the formula (II'):

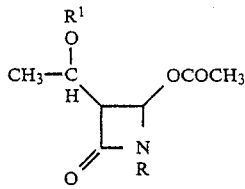 (II')

wherein $R^1$ and R are as above. In the above reaction, the kinds of base and solvent employed and the reaction temperature affect the yield of the desired compound. A halogenated hydrocarbon or an aromatic hydrocarbon, preferably a halogenated hydrocarbon such as methylene chloride can be employed as a reaction solvent. The most preferable base is dimethylaminopyridine, which may also be used in combination with other bases such as pyridine, lutidine and picoline. The amount of the base employed is 1 to 5 times moles, preferably 1 to 3 times moles of the β-lactam compound having the formula (I) and the amount of acetic anhydride employed as a reagent for introducing acetoxyl group is 1 to 20 times moles, preferably 3 to 15 times moles of the β-lactam compound.

The reaction is carried out in an organic solvent such as methylene chloride by adding dimethylaminopyridine and acetic anhydride to the β-lactam compound having the formula (I) and stirring the mixture at a temperature of −50° C. to room temperature, preferably at a temperature of −30° to 5° C. until the compound having the formula (I) disappears. When another base such as pyridine or picoline is added in addition to dimethylaminopyridine, the yield is improved. After the reaction is completed, an extraction solvent such as methylene chloride or hexane is added to the reaction mixture, and thereto an aqueous solution of sodium hydrogen carbonate is added. Then the organic layer is separated from the reaction mixture, washed with water. After dehydration, the organic solvent is distilled away to give the N-protected β-lactam compound having an acetoxyl group at the C4-position. The obtained compound having the formula (II') is subjected to the next reaction where the N-protective group is removed. If desired, this compound (II') can be purified by means of silica-gel column chromatography.

When the N-protective group is removed, it is required that only N-protective group is selectively removed without removal of the O-protective group of hydroxyethyl group at the C3-position. For example, tetrabutylammonium fluoride or tetramethylammonium fluoride is preferably used when the N-protective group is an alkylsilyl group such as tert-butyldimethylsilyl group. A reagent obtained by combining a quarternary ammonium halide such as tetrabutylammonium chloride, tetrabutylammonium bromide, tetramethylammonium chloride or trimethylbenzylammonium chloride with potassium fluoride has an equivalent effect to tetrabutylammonium fluoride or tetramethylammonium fluoride. When methanol is used as the solvent, potassium fluoride alone can be employed as a reagent.

The solvent used in removing the N-protective group is preferably tetrahydrofuran, acetonitrile or methylene chloride and the reaction is smoothly proceeded by stirring at room temperature. It causes the improvement of the yield to carry out the above reaction in the presence of acetic acid. After the reaction is completed, an extraction solvent such as ethyl acetate is added to the reaction mixture, and thereto a dilute alkali solution is added. Then, the organic layer is extracted, washed with water, dehydrated and dried, and finally the organic solvent is distilled away to give the desired compound of a 4-acetoxy-3-hydroxyethylazetidin-2-one derivative. The 4-acetoxy-3-hydroxyethylazetidin-2-one derivative can be purified by crystallization from n-hexane or petroleum ether, or by silica-gel column chromatography.

The present invention is more particularly explained by the following non-limiting examples. However, it is to be understood that any modification or development can be made without departing from the scope and spirit of the present invention.

EXAMPLE 1

[Preparation of (3R,4R)-4-acetoxy-3-[(R)-1-tert-butyldimethylsilyloxyethyl]-azetidin-2-one]

There was dissolved 1.0 g of (3R,4R)-3-(1-tert-butyldimethylsilyloxyethyl)-4-trimethylsilyloxyazetidin-2-one in 10 ml of DMF, to which 0.89 g of triethylamine and 0.61 g of tert-butyldimethylsilyl chloride were added and the mixture was stirred for 9 hours at room temperature. After the reaction was completed, DMF was distilled away under reduced pressure and thereto 30 ml of hexane was added. After the solution was washed successively with 2.5% aqueous solution of $NaHCO_3$, an aqueous solution of hydrochloric acid of pH 3 and saturated solution of salt and dried with magnesium sulfate, the solvent was distilled away to give 1.24 g of liquid of a crude product. There was added 1 g of the liquid obtained above to 5 ml of methylene chloride, thereto 0.85 g of dimethylaminopyridine and 1.1 ml of acetic anhydride was added, and the mixture was reacted for 6 hours at room temperature. After the reaction mixture was washed successively with 5% aqueous solution of $NaHCO_3$, an aqueous solution of hydrochloric acid of pH 3 and saturated solution of salt and dried with magnesium sulfate, the solvent was distilled away to give 0.8 g of a liquid crude product. The liquid was purified by means of silica-gel column chromatography (benzene:hexane=2:1) to give 0.5 g of (3R,4R,5R)-4-acetoxy-1-(tert-butyldimethylsilyl)-3-(1-tert-butyldimethylsilyloxyethyl)-azetidin-2-one as a liquid.

There was added 0.5 g of the liquid to 2 ml of THF (tetrahydrofuran), to which 0.4 g of tetrabutylammonium fluoride, and 0.17 g of acetic acid in 2 ml of THF solution was added and the mixture was stirred for 30 minutes at room temperature. After adding 20 ml of ethyl acetate to the reaction mixture, the resultant was washed successively with 5% aqueous solution of $NaHCO_3$ and saturated solution of salt and dried with magnesium sulfate. The solvent was distilled away to give 0.30 g of the desired compound as crystals. The obtained crystals were purified by means of silica-gel column chromatography (benzene:ethyl acetate=6:1) to give 0.27 g of the desired β-lactam compound as a solid. The obtained β-lactam compound had the following properties.

mp: 107° to 108° C.
$[\alpha]_D^{25} = +50°$ (C=0.5 $CHCl_3$)

$^1$HNMR (90 MHz, $CDCl_3$) δ(ppm) 0.08 (6H, s), 0.84 (9H, s), 1.20 (3H, d), 2.01 (3H, s), 3.04 (1H, dd), 4.12 (1H, m), 5.76 (1H, d) and 6.73 (NH)

EXAMPLE 2

[Preparation of (3R,4R)-4-acetoxy-3-[(R)-1-tert-butyldimethylsilyloxyethyl]-azetidin-2-one]

There was dissolved 1 g of (3R,4R)-1-tert-butyldimethylsilyl-3-[(R)-1-tert-butyldimethylsilyloxyethyl]-4-trimethylsilyloxyazetidin-2-one into 10 ml of methylene chloride, thereto 0.85 g of dimethylaminopyridine and 0.71 g of acetic anhydride were added and the mixture was reacted for one day at 0° C. After the reaction mixture was diluted with hexane and washed successively with 5% aqueous solution of $NaHCO_3$, an aqueous solution of hydrochloric acid of pH 4 and saturated solution of salt, the resultant was dried with magnesium sulfate and the solvent was distilled away to give 0.85 of a liquid crude product. The obtained liquid was purified by a silica-gel column chromatography (hexane:ether=30:1) to give 0.40 g of (3R,4R)-4-acetoxy-1-tert-butyldimethylsilyl)-3-[(R)-1-tert-butyldimethylsilyloxyethyl)azetidin-2-one as a colorless liquid.

There was added 2 ml of THF to the obtained liquid, thereto 0.26 g of tetrabutylammonium fluoride and 0.12 g of acetic acid in 2 ml of THF were added and the mixture was stirred for 30 minutes at room temperature. After adding 20 ml of ethyl acetate to the reaction mixture, the resultant was washed successively with 5% aqueous solution of $NaHCO_3$ and saturated solution of salt, and dried with magnesium sulfate. The solvent was distilled away to give 0.29 g of a solid. The obtained solid was recrystallized from hexane to give 0.20 g of the desired β-lactam as colorless needles.

The results of melting point, specific rotation and NMR spectrum of the obtained β-lactam compound were the same as those in Example 1.

EXAMPLE 3

[Preparation of (3R,4R)-4-acetoxy-3-[(R)-1-tert-butyldimethylsilyloxyethyl]-azetidin-2-one]

There was dissolved 1 g of (3R,4R)-1-tert-butyldimethylsilyl-3-[(R)-1-tert-butyldimethylsilyloxyethyl]-4-trimethylsilyloxyazetidin-2-one into 10 ml of methylene chloride, thereto 0.85 g of dimethylaminopyridine, 0.75 g of 2,6-lutidine and 1.42 g of acetic anhydride were added and the mixture was reacted for 44 hours at -15° C. After the reaction mixture was diluted with ether and washed successively with 5% aqueous solution of $NaHCO_3$, an aqueous solution of hydrochloric acid of pH 4 and saturated solution of salt, the resultant was dried with magnesium sulfate. The solvent was distilled away to give 0.88 g of a liquid crude product. The obtained liquid was purified by means of silica-gel column chromatography (hexane:ethyl acetate=100:1) to give 0.58 g of (3R,4R)-4-acetoxy-tert-butyldimethylsilyl)-3-[(R)-1-tert-butyldimethylsilyloxyethyl]azetidin-2-one as a liquid.

There was dissolved the obtained liquid into 2 ml of THF, thereto 0.38 g of tetrabutylammonium fluoride and 0.17 g of acetic acid in 2 ml of THF was added and the mixture was stirred for 30 minutes at room temperature. After adding 20 ml of ethyl acetate to the reaction mixture, the resultant was washed successively with 5% aqueous solution of $NaHCO_3$ and saturated solution of salt, and dried with magnesium sulfate. The solvent was distilled away to give 0.42 g of a solid. The obtained solid was purified by silica-gel column chromatography (hexane:ether=10:3) to give 0.39 g of the desired β-lactam as colorless needles.

The results of melting point, specific rotation and NMR spectrum of the obtained β-lactam were the same as those in Example 1.

EXAMPLE 4

[Preparation of (3R,4R)-4-acetoxy-3-[(R)-1-isopropyldimethylsilyloxyethyl]-azetidin-2-one]

There was dissolved 1.2 g of 3-[(R)-1-isopropyldimethylsilyloxyethyl]-4-trimethylsilyloxyazetidin-2-one ((3R,4R,5R)-form:(3S,4S,5R)-form=5:1) into 12 ml of DMF, thereto 0.52 g of triethylamine and 0.79 g of tert-butyldimethylsilyl chloride were added and the mixture was stirred for 9 hours at room temperature. After the reaction was completed, DMF was distilled away under reduced pressure and thereto 30 ml of hexane was added. After the reaction mxiture was washed successively with 2.5% aqueous solution of NaHCO₃, an aqueous solution of hydrochloric acid of pH 5 and saturated solution of salt, and was dried with magnesium sulfate, the solvent was distilled away to give 1.13 g of a liquid crude product.

There was added 0.90 g of the obtained liquid to 10 ml of methylene chloride, thereto 0.79 g of dimethylaminopyridine and 0.61 ml of acetic anhydride were added and the mixture was reacted for 16 hours at 4° C. After the reaction mixture was washed successively with 5% aqueous solution of NaHCO₃, an aqueous solution of hydrochloric acid of pH 5 and saturated solution of salt, and dried with magnesium sulfate, the solvent was distilled away to give 0.70 g of a liquid crude product. The obtained liquid was purified by means of silica-gel column chromatography (hexane:ether=100:3) to give 0.20 g of 4-acetoxy-1-tert-butyldimethylsilyl)-3-(1-isopropyldimethylsilyloxyethyl)azetidin-2-one as a liquid.

There was added 0.20 g of the obtained liquid to 2 ml of THF, thereto 0.13 g of tetrabutylammonium fluoride and 0.03 g of acetic acid in 2 ml of THF was added and the mixture was stirred for 30 minutes at room temperature. There was added 60 ml of ethyl acetate to the reaction mixture and the mixture was washed successively with 5% aqueous solution of NaHCO₃ and saturated solution of salt, and dried with magnesium sulfate. The solvent was distilled away to give 0.14 g of a crude product ((3R,4R,5R)-form:(3S,4S,5R)-form=5:1). The crude product was recrystallized from hexane to give 0.58 g of the desired product of (3R,4R,5R)-form as white crystals.

The obtained β-lactam compound had the following properties. (3R,4R,5R)-form

¹HNMR (90 MHz, CDCl₃) ((3R,4R,5R)-form) δ(ppm): 0.04 (6H, s), 0.90 (7H), 1.23 (3H, d), 2.06 (3H, s), 3.13 (1H, dd), 4.13 (1H, m), 5.76 (1H, d) and 6.40 (NH)
[α]$_D^{25}$= +54.2° (C=0.5, CHCl₃)
mp: 92° to 94° C.

EXAMPLE 5

[Preparation of (3R,4R)-4-acetoxy-3-[(R)-1-(dimethyl-1,1,2-trimethylpropylsilyloxy)ethyl]-azetidin-2-one]

There was dissolved 0.98 g of (3R,4R)-3-[1-(dimethyl-1,1,2-trimethylpropylsilyloxy)ethyl]-4-trimethylsilyloxy-azetidin-2-one to 5 ml of methylene chloride and thereto 0.58 g of triethylamine and 0.66 g of dimethyl-1,1,2-trimethylpropylsilyl chloride were added, and the mixture was stirred for 9 hours at room temperature. After completion of the reaction, the resultant mixture was washed with an aqueous solution of hydrochloric acid of pH 4 and the solvent was distilled away under reduced pressure to give 1.28 g of a liquid crude product. There was added 1.27 g of the obtained liquid to 6 ml of methylene chloride, and thereto 0.95 g of dimethyl aminopyridine and 1.59 g of acetic anhydride were further added, and the mixture was reacted for 46 hours at −15° C. After the reaction mixture was washed with 5% aqueous solution of NaHCO₃ and then water, the organic layer was separated and the solvent was distilled away under reduced pressure to give 1.27 g of a liquid crude product. There was dissolved 1.19 g of the obtained liquid in 6 ml of methylene chloride, and to which 0.6 g of tetramethylammonium chloride and 0.3 g of potassium fluoride and 0.68 g of acetic acid were added, and the mixture were stirred for 2 hours at room temperature. After completion of reaction, the resultant mixture was washed with 5% aqueous solution of NaHCO₃ and then water, and the organic layer was separated and was condensed under reduced pressure to give 0.7 g of a solid crude product. Then, the obtained solid was recrystallized from hexane to give 0.35 g of the desired β-lactam compound as a solid.

The obtained β-lactam compound had the following properties.
mp: 80° to 81° C.
[α]$_D^{25}$= +41.6° (c=0.5, CHCl₃)
¹HNMR (90 MHz, CDCl₃) δ(ppm): 0.08 (6H, s), 0.65 (6H, s), 0.75 (6H, d), 1.15 (3H, d), 1.40 (1H, m), 2.08 (3H, s), 3.00 (1H, dd), 4.10 (1H, m), 5.71 (1H, d), 6.60 (NH)

What we claim is:

1. A process for preparing a 4-acetoxy-3-hydroxyethylazetidin-2-one derivative having the formula (II):

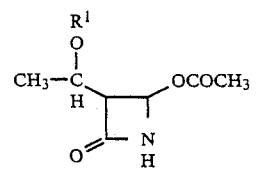

wherein R¹ is a protective group for the hydroxyl group, which comprises reacting a β-lactam compound having the formula (I):

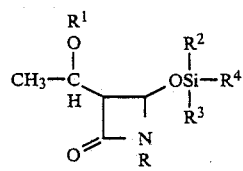

wherein R¹ is as defined above, and each of R², R³ and R⁴ is independently a lower alkyl group having 1 to 4 carbon atoms, phenyl group or an aralkyl group and R is a protective group for N, with acetic anhydride in an organic solvent in the presence of a base at a temperature ranging from −30° C. to 5° C., and removing the protective group for N, the proportion of acetic anhydride to said β-lactam compound (I) being 1:1 to 20:1, and the proportion of said base to said β-lactam compound (I) being 1:1 to 5:1.

2. The process of claim 1, wherein R¹ is a group of the formula (III):

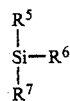     (III)

wherein each of R⁵, R⁶ and R⁷ is independently a lower alkyl group having 1 to 4 carbon atoms.

3. The process of claim 1, wherein R¹ is t-butyldimethylsilyl.

4. The process of claim 1, wherein R¹ is isopropyldimethylsilyl.

5. The process of claim 1, wherein R is t-butyldimethylsilyl.

6. The process of claim 1, wherein each of R², R³ and R⁴ is methyl.

7. The process of claim 1, wherein the base is dimethylaminopyridine.

8. A process for preparing a 4-acetoxy-3-hydroxyethylazetidin-2-one derivative having the formula (II):

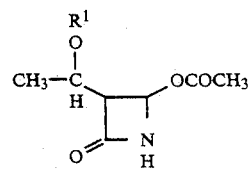     (II)

wherein R¹ is a protective group for the hydroxyl group, which comprises reacting a β-lactam compound having the formula (I):

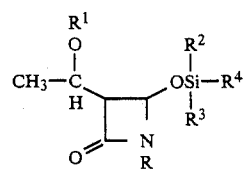     (I)

wherein R¹ is as defined above, and each of R², R³ and R⁴ is independently a lower alkyl group having 1 to 4 carbon atoms, phenyl group or an aralkyl group, and R is a protective group for N, with acetic anhydride in an organic solvent in the presence of dimethylaminopyridine in combination with at least one other base, at a temperature ranging from −30° C. to 5° C., and removing the protective group for N, the proportion of acetic anhydride to said β-lactam compound (I) being 1:1 to 20:1, and the proportion of said base to said β-lactam compound (I) being 1:1 to 5:1.

9. The process of claim 8, wherein said other base is a member selected from the group consisting of pyridine, lutidine and picoline.

10. The process of claim 1, wherein the organic solvent is a halogenated hydrocarbon.

11. A process for preparing a 4-acetoxy-3-hydroxyethylazetidin-2-one derivative having the formula (II):

     (II)

wherein R¹ is a protective group for the hydroxyl group, which comprises reacting a compound having the formula (I'):

(I')

wherein R¹ is as defined above, and each of R², R³ and R⁴ is independently a lower alkyl group having 1 to 4 carbon atoms, phenyl group or an aralkyl group, with a reagent having the formula R—X, wherein R is a protective group for N and X is a halogen atom, to form a β-lactam compound having the formula (I):

(I)

wherein R, R¹, R², R³ and R⁴ are as defined above, reacting the compound (I) with acetic anhydride in an organic solvent in the presence of a base at a temperature ranging from −30° C. to 5° C., and removing the protective group for N, the proportion of acetic anhydride to said β-lactam compound (I) being 1:1 to 20:1, and the proportion of said base to said β-lactam compound (I) being 1:1 to 5:1.

12. The process of claim 11, wherein R¹ is a group of the formula (III):

(III)

wherein each of R⁵, R⁶ and R⁷ is independently a lower alkyl group having 1 to 4 carbon atoms.

* * * * *